(12) United States Patent
Atreya et al.

(10) Patent No.: US 12,270,066 B2
(45) Date of Patent: Apr. 8, 2025

(54) METHOD TO SENSE THE PRESENCE AND ACTIVITY OF MICROBES THROUGH THE USE OF TRANSIENT SENSING MATERIALS

(71) Applicant: THE REGENTS OF THE UNIVERSITY OF COLORADO, A BODY CORPORATE, Denver, CO (US)

(72) Inventors: Madhur Atreya, Louisville, CO (US); Gabrielle Marinick, Phoenix, AZ (US); Gregory Whiting, Boulder, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 0 days.

(21) Appl. No.: 18/040,418

(22) PCT Filed: Jul. 30, 2021

(86) PCT No.: PCT/US2021/044062
§ 371 (c)(1),
(2) Date: Feb. 2, 2023

(87) PCT Pub. No.: WO2022/031558
PCT Pub. Date: Feb. 10, 2022

(65) Prior Publication Data
US 2023/0212636 A1 Jul. 6, 2023

Related U.S. Application Data

(60) Provisional application No. 63/060,463, filed on Aug. 3, 2020.

(51) Int. Cl.
*C12Q 1/00* (2006.01)

(52) U.S. Cl.
CPC .................... *C12Q 1/001* (2013.01)

(58) Field of Classification Search
None
See application file for complete search history.

(56) References Cited

U.S. PATENT DOCUMENTS

| | | | |
|---|---|---|---|
| 9,921,219 B2* | 3/2018 | Elias | G01N 33/54373 |
| 2004/0072357 A1 | 4/2004 | Stiene et al. | |
| 2005/0019805 A1 | 1/2005 | Groll | |
| 2008/0085529 A1 | 4/2008 | Imperiali et al. | |
| 2011/0091391 A1 | 4/2011 | Ribi | |
| 2012/0277562 A1 | 11/2012 | Brister et al. | |
| 2018/0208762 A1* | 7/2018 | Pomestchenko | B29C 71/02 |

FOREIGN PATENT DOCUMENTS

WO    2003/012419 A1    2/2003

OTHER PUBLICATIONS

Atreya, Madhur, et al. "Poly (lactic acid)-based ink for biodegradable printed electronics with conductivity enhanced through solvent aging." ACS applied materials & interfaces 12.20 (2020): 23494-23501 (Year: 2020).*
Samrot, Antony V., et al. "The synthesis, characterization and applications of polyhydroxyalkanoates (PHAs) and PHA-based nanoparticles." Polymers 13.19 (2021): 3302. (Year: 2021).*
Wu, Chin-San, Hsin-Tzu Liao, and Yu-Xuan Cai. "Characterisation, biodegradability and application of palm fibre-reinforced polyhydroxyalkanoate composites." Polymer Degradation and Stability 140 (2017): 55-63. (Year: 2017).*
Yang, Li, et al. "Wearable RFID-enabled sensor nodes for biomedical applications." 2008 58th Electronic Components and Technology Conference. IEEE, 2008. (Year: 2008).*
International Search Report and Written Opinion received for PCT Patent Application No. PCT/US21/44062, mailed on Nov. 12, 2021, 7 pages.
Mai et al., "Poly(lactic acid)/carbon nanotube nanocomposites with integrated degradation sensing", Polymer, vol. 53, 2013, pp. 6818-6823.
Bergdahl et al., "Capacitive Sensor to Monitor Enzyme Activity by Following Degradation of Macromolecules in Real Time ", Applied Biochemistry and Biotechnology, Apr. 24, 2019, vol. 189, pp. 374-383.
Fernandez-Sanchez et al., "Electrochemical impedance spectroscopy studies of polymer degradation: Application to biosensor development", Trends in Analytical Chemistry, vol. 24, No. 1, 2005, pp. 37-48.
Lisdat et al., "The use of electrochemical impedance spectroscopy for biosensing", Anal Bioanal Chem., Apr. 16, 2008, vol. 391, pp. 1555-1567.

* cited by examiner

*Primary Examiner* — Robert J Yamasaki
(74) *Attorney, Agent, or Firm* — Workman Nydegger

(57) ABSTRACT

Disclosed are sensors and related methods for measuring enzyme activity in a measurement environment and for quantifying enzyme and/or microbe concentrations in the measurement environment. An enzyme activity sensor includes a degradable conductive trace and a biodegradable target configured to enable the conductive trace, in an initial state, to conduct electrical current between first and second terminal ends via conductive particles. The conductive trace is configured to degrade over time as a result of enzymatic activity that degrades the biodegradable target when the sensor is placed in a measurement environment, the enzymatic activity thereby increasing resistance between the first and second terminal ends.

29 Claims, 5 Drawing Sheets

METHOD TO SENSE THE PRESENCE AND ACTIVITY OF MICROBES THROUGH THE USE OF TRANSIENT SENSING MATERIALS

CROSS-REFERENCE TO RELATED APPLICATIONS

This application is a nationalization of and claims priority to PCT Application No. PCT/US2021/044062, filed Jul. 30, 2021, entitled "Method To Sense The Presence And Quantities Of Microbes Through The Use Of Transient Sensing Materials", which claims priority to and the benefit of U.S. Provisional Patent Application Ser. No. 63/060,463, filed Aug. 3, 2020 and titled "Method to Sense the Presence and Quantities of Microbes Through the Use of Transient Sensing Materials". Each of the aforementioned applications is incorporated by reference herein in their entirety.

BACKGROUND

Technical Field

This disclosure relates to sensors for measuring enzymatic and/or microbial activity and/or concentrations at a measurement location such as an environmental or agricultural location.

Related Technology

Soil enzymes increase the break down of plant residues and subsequent release of nutrients back to the soil. Soil enzymes have important roles in organic matter decomposition and nutrient cycling. The enzyme activity of soil is therefore an important soil quality indicator. Characterizing and successfully monitoring soil enzyme activity is a desirable goal in the art. Successfully determining enzyme activity is key to successfully identifying areas of degradation and successfully monitoring restoration projects. These needs have become more apparent in recent years as soil health has declined in many regions, despite the importance of soil health to food security, ecological function, and the economy at large.

Enzyme activity is typically measured indirectly using various laboratory assays. Standard biochemical assays are typically designed to measure total potential enzyme activity, however, and do not necessarily correspond to true in situ enzyme activity levels.

Accordingly, there is an ongoing need in the art for sensors and methods capable of providing in situ monitoring and measurement of enzyme activity in soils and other environmental or agriculture sites.

SUMMARY

This disclosure is directed to sensor embodiments and related methods for measuring enzyme activity, enzyme and/or microbe concentrations, and biodegradation potential at a measurement location/environment. In one embodiment, a sensor is placed in a measurement environment where enzyme activity is expected or suspected. In one embodiment, the sensor is positioned so that at least a portion of a conductive trace is exposed to the potential enzyme activity and/or microbial activity of the measurement environment.

A biodegradable target portion of the sensor is configured to enable the conductive trace, in an initial state, to conduct electrical current between first and second terminal ends with relatively low resistance. The biodegradable target is configured to degrade in the presence of one or more corresponding target enzymes and/or microbes. Thus, as the sensor continues to reside in the measurement environment and the biodegradable target is further subjected to enzymatic activity from the target enzyme(s) and/or microbe(s), the biodegradable target will degrade and lose its ability to promote conductivity of the conductive trace. As a result, the resistance between the terminal ends will rise. Accordingly, by measuring resistance, one may obtain an indication of the level of degradation of the biodegradable target and thus the level of corresponding enzymatic activity in the measurement environment.

In one embodiment, a method of measuring enzyme activity comprises: providing an enzyme activity sensor, the biodegradable target of the enzyme activity sensor being configured to degrade in the presence of one or more target enzymes; positioning the enzyme activity sensor in a measurement environment having or suspected of having the one or more target enzymes; measuring resistance in the conductive trace of the enzyme activity sensor; determining that the resistance has reached a threshold level indicative of enzymatic degradation of the biodegradable target of the enzyme activity sensor; and based on the time to reach the threshold level indicative of enzymatic degradation of the biodegradable target, determine a level of the one or more target enzymes in the measurement environment.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

DETAILED DESCRIPTION

Enzyme Activity Sensors

Figure 1:
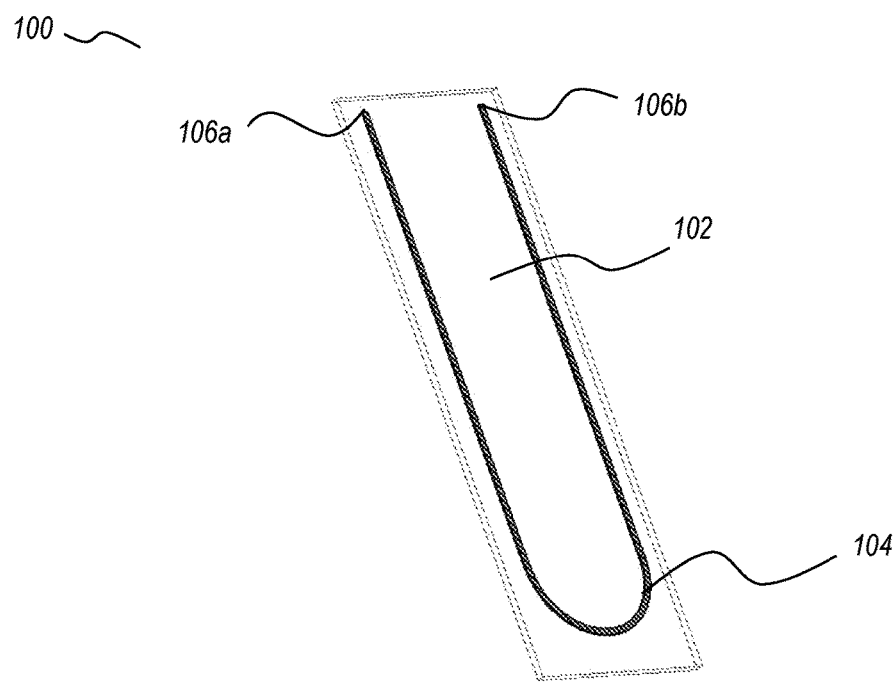
FIG. 1 illustrates an embodiment of an enzyme and/or microbe activity sensor comprising a biodegradable conductive trace on a support.

FIG. 1 illustrates an embodiment of an enzyme activity sensor 100 comprising a biodegradable conductive trace 104 disposed upon a support 102. The conductive trace 104 extends between first and second terminal ends 106a and 106b. An intermediate section is defined as a portion of the conductive trace 104 between the terminal ends 106a and 106b. The illustrated sensor 100 shows a conductive trace 104 with a curved, "U" shape. However, other embodiments may utilize conductive traces of different shapes.

Note that in the following examples, reference will be made to "target enzymes" and "enzyme activity". It will be understood that the same principles and features of these embodiments are readily applicable to measuring, quantifying, and/or monitoring microbial activity from one or more microbes. For simplicity, not every reference will specify that microbial activity may be measured using the disclosed embodiments, but it will be understood that such is the case.

In one example of operation of the sensor 100, the sensor 100 is placed in a measurement environment where enzyme activity is expected or suspected. The sensor 100 is positioned so that at least a portion of the intermediate section of the conductive trace 104 is exposed to the potential enzyme activity of the measurement environment. A biodegradable target is configured to enable the conductive trace 104, in an initial state, to conduct electrical current between the first and second terminal ends 106a and 106b with relatively low resistance. The biodegradable target is configured to degrade in the presence of one or more target enzymes. Thus, as the sensor 100 continues to reside in the measurement environment and the biodegradable target is further subjected to enzymatic activity from the target enzyme(s), the biodegradable target will degrade and lose its ability to maintain conductivity of the conductive trace 104. As a result, the resistance between the terminal ends 106a and 106b will rise. Accordingly, by measuring resistance, one may obtain an indication of the level of degradation of the biodegradable target and thus the level of corresponding enzymatic activity in the measurement environment.

Figure 2:
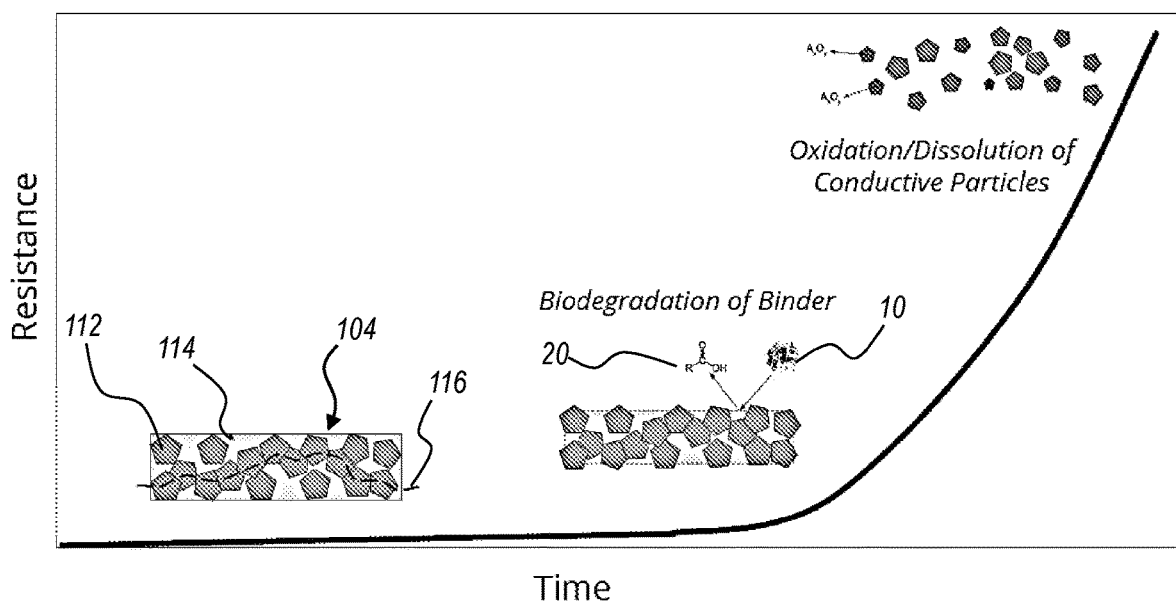
FIG. 2 illustrates operation of the enzyme activity sensor of FIG. 1, showing that resistance increases over time as the conductive trace degrades via enzyme and/or microbe activity and conductive particles held within the trace by a binder dissolute and/or are oxidized.

Now referring to FIG. 2, in the illustrated embodiment, the conductive trace 104 of the sensor 100 includes a biodegradable target in the form of a binder 114 in which conductive particles 112 are held. FIG. 2 schematically illustrates operation of the enzyme activity sensor 100, showing that resistance increases over time as the binder 114 is attacked by target enzyme(s) 10 and converted to byproducts 20. The conductive particles 112 held within the conductive trace 104 by the binder 114 are then increasingly 10 subject to dissolution and/or oxidation.

The binder 114, when sufficiently intact, functions to keep the conductive particles 112 in sufficiently close proximity to maintain percolation pathways 116 and keep resistance relatively low. As the binder 114 degrades, however, the conductive particles 112 are increasingly exposed and subject to dissolution and/or oxidation. This leads to a concomitant increase in the resistance of the conductive trace 104.

Figure 3A:
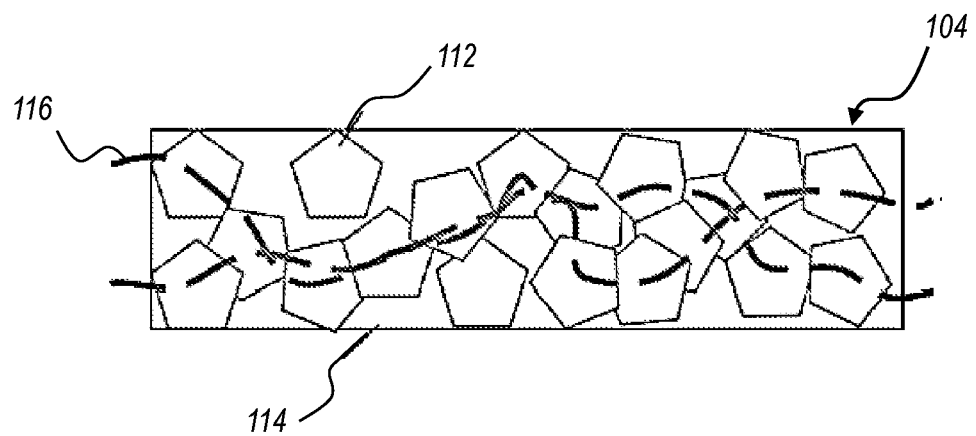
FIGS. 3A-3D illustrate in greater detail the enzymatic degradation of the conductive trace of the enzyme and/or microbe activity sensor of FIG. 1, showing initial swelling of the binder, degradation of the binder, and dissolution and/or oxidation of the conductive particles.

FIGS. 3A-3D illustrate in greater detail the enzymatic degradation of the conductive trace 104 of the enzyme activity sensor 100. FIG. 3A illustrates an initial state of the conductive trace 104. In this state, the binder 114 is intact and the conductive particles 112 are positioned in sufficient density to provide percolation pathways 116 and relatively low resistance through the conductive trace 104.

Figure 3B:
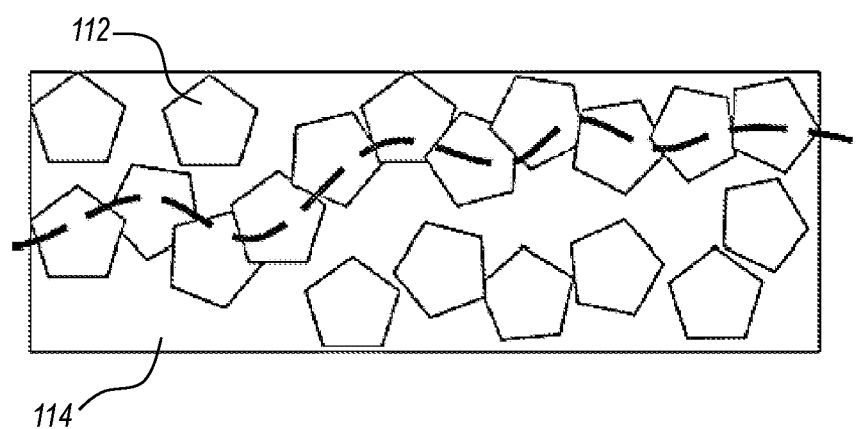

FIG. 3B illustrates the conductive trace 104 after the binder 114 has swollen due to absorption of water. In most embodiments, such water absorption and swelling are acceptable, and sufficient conductivity is maintained through the conductive particles 112 and the overall trace 104. As selection of the binder 114 is not necessarily limited by water absorption properties, this allows a wide variety of biodegradable target materials to be utilized as the binder 114. In certain embodiments, water absorption and swelling are desired. For example, water absorption may aid in bringing target enzymes from the measurement environment into closer proximity with the internal molecules of the binder so as to enable more accurate and/or faster functioning of the sensor 100. Examples of such materials that may be utilized as the binder 114 include oligo- and polysaccharides. Other example materials that may be additionally or alternatively utilized are described in more detail elsewhere herein.

Figure 3C:
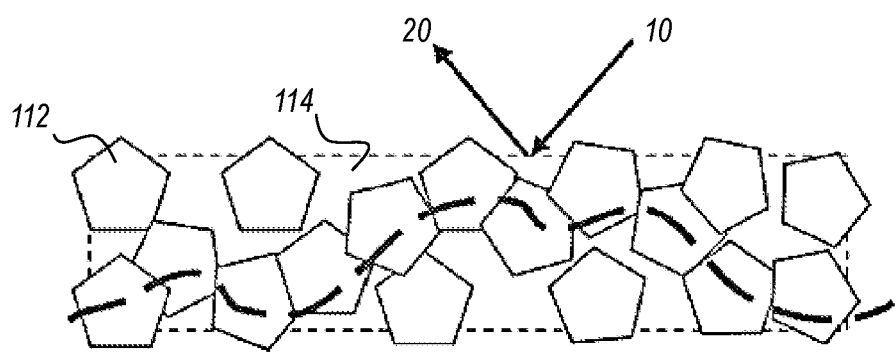

FIG. 3C illustrates degradation of the binder 114 as target enzyme(s) 10 catalyze conversion of the binder 114 into byproducts 20. As the binder 114 degrades as a result of enzymatic activity from the target enzyme(s) 10, the conductive particles 112 become more exposed to the environment. In FIG. 3C, the conductive particles 112 are still able to provide relatively good conductance of current and therefore resistance is still relatively low.

Figure 3D:
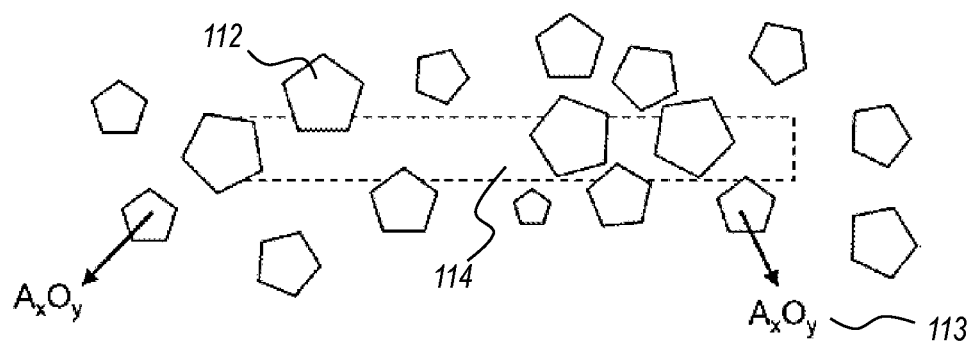

FIG. 3D illustrates even further degradation of the binder 114 and the resulting dissolution of the conductive particles 112. As shown, the conductive pathways provided by the conductive particles 112 begin to fall apart as particles 112 disassociate and disperse. In addition, the increased exposure to the surrounding environment will typically lead to increased oxidation of the conductive particles 112, causing conversion to less conductive oxidation products 113.

Referring back to FIG. 1, the support 102 may be formed from any material sufficiently durable for supporting the conductive trace 104. The support 102 may be formed from a plastic or other polymer material, wood, glass, metal, or ceramic. In some embodiments, the support 102 is itself biodegradable and/or suitable for long-term placement in the environment (e.g., wood).

The enzyme activity sensors and related systems and methods described herein may be beneficially utilized in a variety of measurement environments. Measurement environments include any location where activity of one or more target enzymes is expected or suspected and where monitoring of the enzyme activity is desired. Examples include environmental monitoring applications such as water (e.g., waterways or water treatment facilities), soil, or wetlands monitoring. Other examples include monitoring of composting, silage, landfill, or food processing operations. Applications could include consumer products such as but not limited to home food spoilage tests. Certain embodiments are particularly well-suited for remote sensing applications such as remote environmental monitoring or remote agricultural monitoring.

Typically, the measured "enzyme activity" is a result of microbial populations in the measurement environment, and any "enzyme target" may therefore include a microbe or set of microbes in lieu of or in addition to specific enzymes. The disclosed embodiments are not necessarily limited to applications where the enzyme activity is caused by microbes, however. Certain laboratory testing or food processing applications, for example, may utilize the described embodiments in conjunction with one or more isolated enzymes. Other embodiments include applications where the biodegradable target is consumed or otherwise degraded by one or more target microbes via a non-enzymatic method.

In use, the portion of the sensor 100 comprising the intermediate section is typically positioned so as to be in more direct contact with the target enzyme, while the terminal ends 106a and 106b remain accessible. For example, with reference to the embodiment of FIG. 1, the "bottom" of the sensor 100 may be placed in soil (or water, etc.) while the terminal ends 106a and 106b stick up and are accessible for electrical connections for making resistance measurements.

Figure 4:
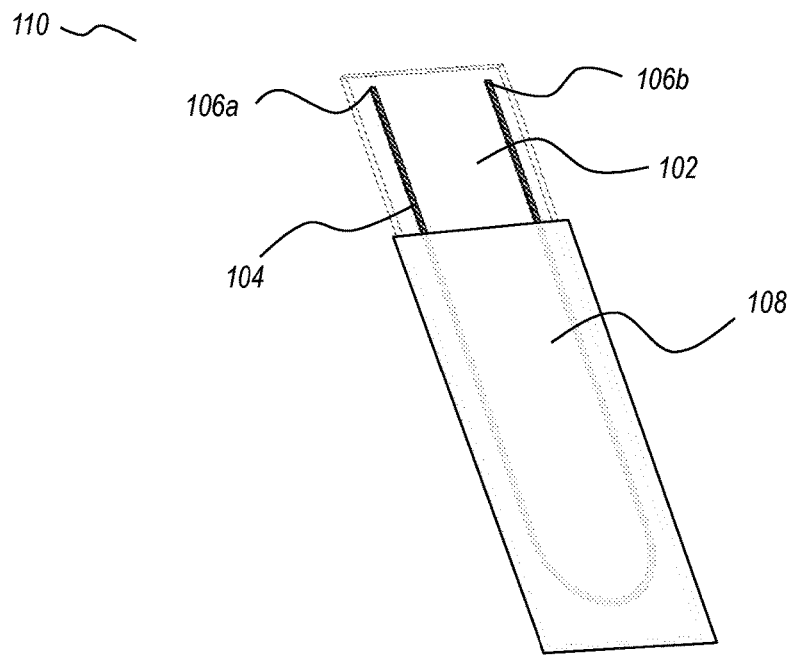
FIG. 4 illustrates another embodiment of an enzyme activity sensor comprising a water-soluble conductive trace encapsulated in a biodegradable encapsulant.

FIG. 4 illustrates another embodiment of an enzyme activity sensor 110. Except as specified below, the sensor 110 is similar to the sensor 100 of FIGS. 1-3D, and thus the features described above in relation to the sensor 100 are also applicable to the sensor 110.

Like sensor 100, the sensor 110 of FIG. 4 includes a support 102 and conductive trace 104 extending between first and second terminal ends 106a and 106b. In the illustrated sensor 110, however, the biodegradable target is not the conductive trace itself, but an encapsulant 108 that encapsulates at least a portion of the conductive trace 104 (e.g., the intermediate section). The encapsulant 108 is formed from a biodegradable material that degrades over time when exposed to one or more target enzymes that act upon the biodegradable material.

In the illustrated configuration, the conductive trace 104 need not be made from a material that is degraded by the same one or more target enzymes of the encapsulant 108. In some embodiments, for example, at least the intermediate section of the conductive trace 104 is formed from a water-soluble polymer. In an initial state, the encapsulant 108 prevents water from reaching the water-soluble polymer of the conductive trace 104 and thereby enables relatively low resistance through the conductive trace 104. In such embodiments, the encapsulant 108 is preferably made from a material that has minimal water absorption so as to minimize water contact with the underlying portions of the conductive trace 104 until the encapsulant 108 has degraded by action of the target enzyme(s). Examples of such materials include waxes and certain thermoset polymers such as polyethylene, Other suitable materials are described elsewhere herein.

Figure 5:
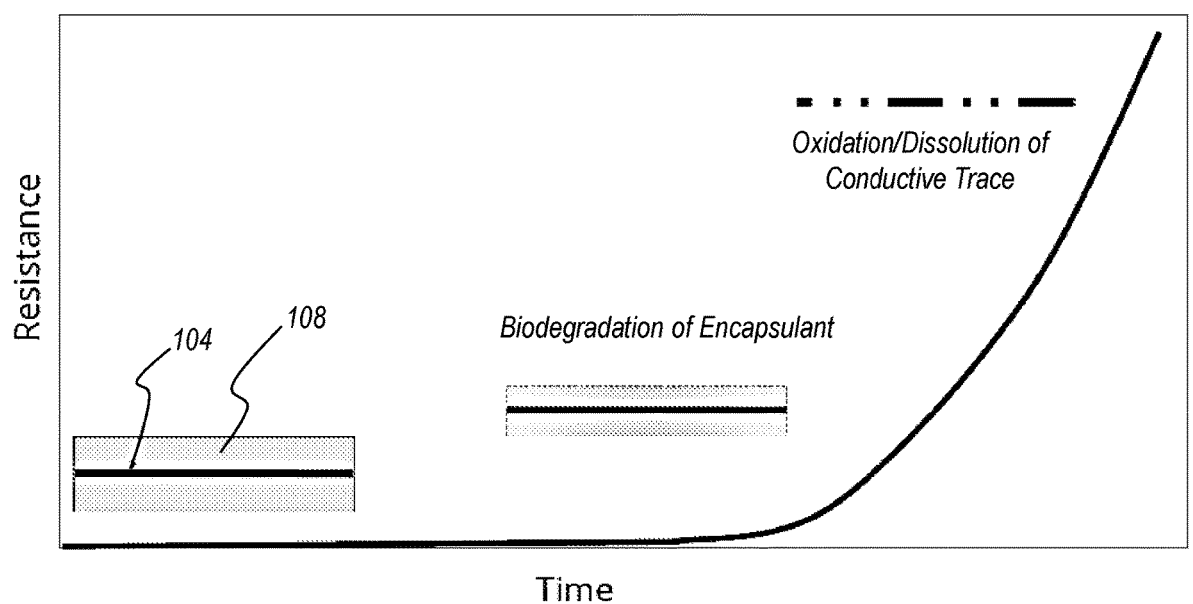
FIG. 5 illustrates operation of the enzyme activity sensor of FIG. 4, showing that resistance increases over time as the biodegradable encapsulant is degraded by enzyme and/or microbe activity and the water-soluble conductive trace is thereby exposed.

FIG. 5 illustrates operation of the enzyme activity sensor 110 of FIG. 4, showing that resistance increases over time as the biodegradable encapsulant 108 is degraded by enzyme activity and the underlying water-soluble conductive trace 104 is thereby exposed to moisture from the measurement environment. As shown, once the encapsulant 108 has sufficiently degraded, the exposed conductive trace 104 is subject to dissolution and/or oxidation. This breaks up the conductive pathways of the conductive material (e.g., particles) and leads to increased resistance measurements.

The water-soluble polymer of the conductive trace 104, when provided in such a configuration, may be formed from any suitable polymer or combination thereof that provides water solubility and breaking up of the conductive trace 104 when exposed to moisture levels expected in the measurement environment. Examples include polyvinyl alcohol (PVA), polyvinylpyrrolidone (PVP), a cellulose derivative, polyethylene oxide (PEO), or combinations thereof. Cellulose derivatives include, for example, hydroxypropyl methylcellulose (HPMC), methyl cellulose, carboxymethyl cellulose, ethyl cellulose, hydroxypropyl cellulose, and hydroxyethyl cellulose.

Figure 6:
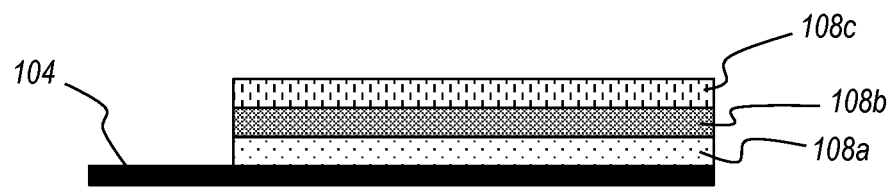
FIG. 6 illustrates an alternative embodiment of an enzyme activity sensor comprising a water-soluble conductive trace encapsulated in a multi-layered biodegradable encapsulant.

FIG. 6 illustrates an alternative embodiment of the enzyme activity sensor 110 comprising a water-soluble conductive trace 104 encapsulated in a multi-layered biodegradable encapsulant with layers 108a, 108b, and 108c. Each layer may be formed from a different biodegradable material subject to degradation by a different target enzyme or set of enzymes. Such multi-layered embodiments thus enable the design of sensors for monitoring sequential and/or combination degradation pathways in a measurement environment. Such multi-layered embodiments can also enable the use of relatively more hydrophilic/absorbent biodegradable target materials by, for example, placing more hydrophilic/absorbent layer(s) toward the inside, closer to the conductive trace 104, while the less hydrophilic/absorbent layer(s) are positioned toward the outside.

The enzyme activity sensors described herein (including sensor 100 and sensor 110) may include conductive traces 104 with conductive particles 112 formed from carbon (e.g., carbon flakes) or a metal (e.g., zinc, tungsten, magnesium, iron). The conductive particles 112 are sized so as to provide sufficient conductive pathways when the conductive trace 104 is in an initial state, but to appropriately disassociate once degradation of the conductive trace 104 has progressed. In some embodiments, for example, the conductive particles 112 may have an average size of about 1 μm to about 50 μm, or about 2 μm to about 25 μm, or about 3 μm to about 12 μm, or a size range with endpoints defined by any two of the foregoing values.

Target Enzymes & Biodegradable Targets

As discussed above, an enzyme activity sensor may be tailored to measure activity of one or more target enzymes by forming the biodegradable target of the sensor from a material known to degrade in the presence of the one or more target enzymes (or at least to degrade at a faster rate in the presence of the one or more target enzymes). The biodegradable target may be provided in the form of a binder in which the conductive particles are disposed to form the conductive trace (as with sensor 100) or alternatively in the form of an encapsulant that encapsulates at least a portion of the intermediate section and protects the underlying portions of the conductive trace from exposure to moisture in the measurement environment (as with sensor 110).

Table 1 lists exemplary groups of target enzymes and corresponding biodegradable targets. This list is not exhaustive. Sensors that utilize other groupings of target enzymes and corresponding biodegradable targets may be determined by those of skill in the art when combined with the additional teachings of the present disclosure.

TABLE 1

Target Enzymes and Corresponding Biodegradable Targets

| Enzyme | Biodegradable Material |
| --- | --- |
| cellobiohydrolase | Cotton, unbleached kraft paper, filter paper |
| β-glucosidase | Cellobiose, cellulose |
| β-xylosidase | Xylooligosaccharides, hemicellulose |
| phenol oxidase | Lignin, lignocellulosic mass, polyethylene |
| Peroxidase (e.g., | Petroleum hydrocarbons, hemicellulose, |

TABLE 1-continued

Target Enzymes and Corresponding Biodegradable Targets

| Enzyme | Biodegradable Material |
|---|---|
| horseradish) | polyethylene, polystyrene, lignin glutaraldehyde |
| chitinase | Chitin, chitosan |
| chitin deacetylase | Chitosan |
| urease | Polyurethane |
| phosphatase | Phosphate monomer esters, phosphate minerals, phytates |
| cutinase | Polyvinyl esters, PET, PCL |
| PHB-depolymerase | Polyhydroxyalkanoates (e.g., PHB, PHBV) |
| lipase | PCL |
| lipolase | Polyacrylates |
| pancrease | Polyacrylates |
| xanthine oxidase | Polyurethanes |
| catalase | Polyurethanes |
| Esterase (e.g., cholesterol esterase) | PET, polyurethanes |
| pullulanase | Certain starch-based polymers |
| Amylase (e.g., alpha, gluco) | Certain starch-based polymers |

In some embodiments, the biodegradable target comprises one or more of a lignin, oligo- or polysaccharide, wax, polyhydroxyalkanoate, fatty acid or fatty acid ester, alkane, polyester, copolyester, polyurethane, polyvinyl ester, or polyacrylate.

In some embodiments where the biodegradable target is an oligo- or polysaccharide, the oligo- or polysaccharide comprises one or more of cellulose, cellobiose, hemicellulose, cellulose derivative, xylooligosaccharide (XOS), fructooligosaccharide (FOS), galactooligosaccharide (GOS), isomaltooligosaccharide (IMO), inulin, chitin, chitosan, alginate, carrageenan, or a starch-based polymer.

In some embodiments where the biodegradable target is a wax, the wax comprises one or more of paraffin wax, beeswax, or soy wax. In some embodiments where the biodegradable target is a fatty acid or ester thereof, the fatty acid or ester thereof comprises palmitate. In some embodiments where the biodegradable target is includes an alkane, the target includes one or more of nonacosane, hexadecane, or octadecane.

In some embodiments where the biodegradable target is a polyester, the target comprises one or more of polycaprolactone (PCL), polyethylene terephthalate (PET), polylactic acid (PLA), or polyglycolic acid (PGA). In some embodiments where the biodegradable target is a polyvinyl ester, the target comprises one or both of polyvinyl acetate or polyvinyl propionate. In some embodiments where the biodegradable target is a polyacrylate, the target comprises one or more of polymethyl acrylate, polyethyl acrylate, or polybutyl acrylate. In some embodiments where the biodegradable target is a copolyester, the target comprises poly(butylene adipate-co-butylene furandicarboxylate).

In some embodiments, the binder comprises one or more petroleum hydrocarbons. In some embodiments, the binder comprises one or more of cotton or paper.

Enzyme Measurement System

Figure 7:
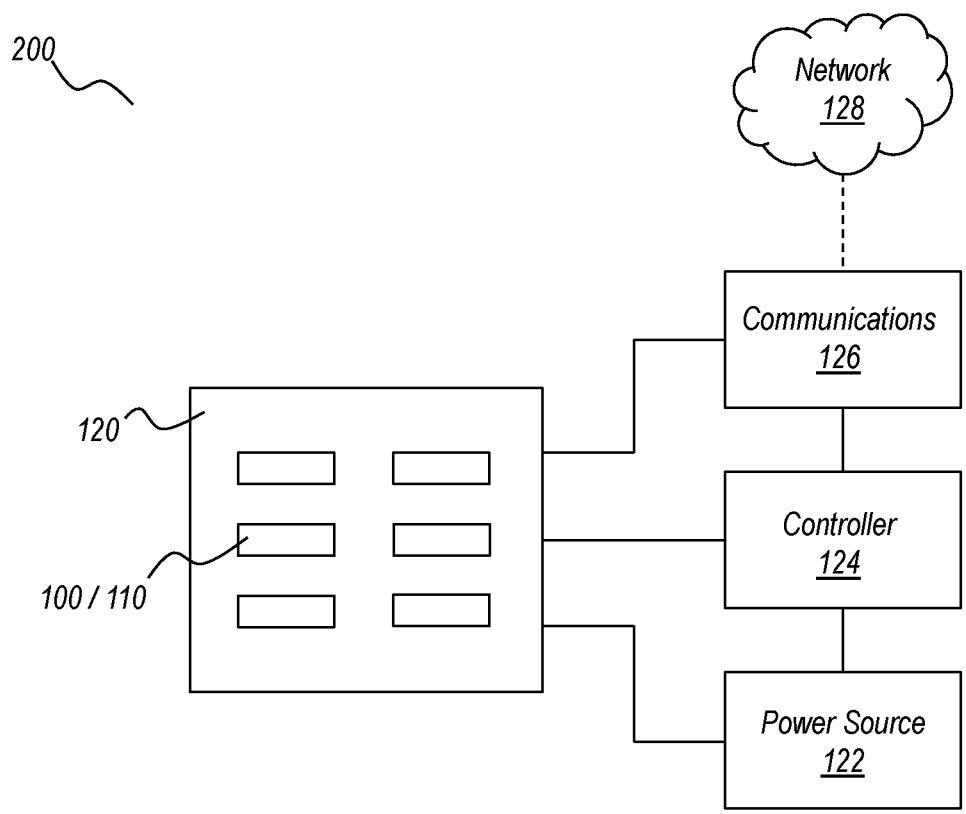
FIG. 7 illustrates an enzyme activity sensor system comprising a panel of multiple enzyme activity sensors and additional components to enable operation of the sensor panel.

FIG. 7 illustrates an exemplary enzyme activity sensor system 200. This embodiment includes a panel 120 of multiple enzyme activity sensors 100 and/or 110. Some embodiments may include a panel 120 with multiple sensors 100 and/or 110 configured for sensing multiple different enzyme targets within the same measurement environment over substantially the same time period.

The illustrated system 200 includes additional components that enable operation of the sensor panel 120 at the site of the measurement environment, which may be, for example, a remote environmental site, agriculture site, or other remote site. As shown, the system 200 may include a power source 122 coupled to the sensor panel 120.

In some embodiments, the power source 122 may include a solar panel, batteries, and/or other components suitable for a remote sensing application.

The illustrated system 200 also includes a controller 124 in electrical communication with the sensor panel 120, the controller 124 being configured to deliver electrical current to the sensors 100/110 of the sensor panel 120 to measure resulting resistance. In other words, the controller 124 can include ohmmeter functionality. The controller 124 may also include a processor and memory to enable programmed or programmable control over measurement frequency, communication protocols, reporting intervals, and the like.

The illustrated system 200 also includes a communications module 126 communicatively connected to the controller 124 and configured to connect to a network 128 to enable transfer of sensor data and/or receipt of system instructions. In some embodiments, the network 128 is a cellular network or a satellite network, for example, though in other embodiments the network 128 is a Local Area Network ("LAN"), a Wide Area Network ("WAN"), or the Internet, for example.

Methods of Measuring Enzyme Activity

As mentioned above, the sensors and systems described herein may be beneficially utilized to measure enzyme activity, enzyme and/or microbe concentrations, and biodegradation potential of a measurement environment in which an enzyme activity sensor and/or system is placed and operated. In one embodiment, a method of measuring enzyme activity comprises the steps of: providing an enzyme activity sensor as in any one of claims 1-29, the biodegradable target of the enzyme activity sensor being configured to degrade in the presence of one or more target enzymes; positioning the enzyme activity sensor in a measurement environment having or suspected of having the one or more target enzymes; measuring resistance in the conductive trace of the enzyme activity sensor; determining that the resistance has reached a threshold level indicative of enzymatic degradation of the biodegradable target of the enzyme activity sensor; and based on the time to reach the threshold level indicative of enzymatic degradation of the biodegradable target, determine a level of the one or more target enzymes in the measurement environment.

In some embodiments, determining the level of the one or more target enzymes in the measurement environment includes calculating a concentration of the one or more target enzymes (and/or one or more microbes associated therewith). These calculations may utilize standard curves or other known methods of sensor calibration. For example, the "time to failure" (i.e., the sensor operating time until reaching the threshold level of resistance) may be determined at various known target enzyme and/or microbe concentrations, and this data may be utilized to generate a standard curve of failure time against concentration.

The threshold level of resistance may be equal or substantially equal to the resistance of a completely open circuit. Alternatively, the threshold level may be set at some other predetermined value that is higher than the initial resistance of the conductive target. Preferably, the threshold level is high enough above the initial baseline as to be indicative of enzymatic degradation of the biodegradable target rather than noise.

Additional Exemplary Embodiments

The following are presented by way of example. Features described in one embodiment may be substituted for, or combined with, features of any other embodiment.

Embodiment 1: A sensor configured for measuring enzyme activity, the sensor comprising: a degradable conductive trace that includes a first terminal end, a second terminal end, and an intermediate section disposed between the first and second terminal ends, the intermediate section including conductive particles disposed therein, a biodegradable target configured to enable the conductive trace, in an initial state, to conduct electrical current between the first and second terminal ends via the conductive particles, and wherein at least the intermediate section is configured to degrade over time as a result of enzymatic activity that degrades the biodegradable target when the sensor is placed in a measurement environment, the enzymatic activity thereby increasing resistance between the first and second terminal ends; and a support upon which the conductive trace is disposed.

Embodiment 2: The sensor of Embodiment 1, wherein the biodegradable target comprises a binder in which the conductive particles are disposed, the binder being formed from a biodegradable material that degrades over time when exposed to one or more enzymes that act upon the biodegradable material.

Embodiment 3: The sensor of Embodiment 2, wherein the binder is not water-soluble.

Embodiment 4: The sensor of Embodiment 2 or 3, wherein the binder absorbs water and swells when exposed thereto.

Embodiment 5: The sensor of Embodiment 1, wherein the intermediate section of the conductive trace comprises a water-soluble polymer in which the conductive particles are disposed, and wherein the biodegradable target comprises an encapsulant that encapsulates the intermediate section, the encapsulant being formed from a biodegradable material that degrades over time when exposed to one or more enzymes that act upon the biodegradable material.

Embodiment 6: The sensor of Embodiment 5, wherein the encapsulant prevents, in an initial state, water from reaching the water-soluble polymer of the conductive trace.

Embodiment 7: The sensor of Embodiment 5 or 6, wherein the encapsulant has negligible water absorption.

Embodiment 8: The sensor of any one of Embodiments 5-7, wherein the encapsulant is made from a first material, the sensor further comprising one or more additional encapsulants, each formed of a different material, layered with the first encapsulant.

Embodiment 9: The sensor of any one of Embodiments 5-8, wherein the water-soluble polymer comprises one or more of polyvinyl alcohol (PVA), polyvinylpyrrolidone (PVP), a cellulose derivative, or polyethylene oxide (PEO).

Embodiment 10: The sensor of any one of Embodiments 1-9, wherein the biodegradable target comprises one or more of a lignin, oligo- or polysaccharide, wax, polyhydroxyalkanoate, fatty acid or fatty acid ester, alkane, polyester, copolyester, polyurethane, polyvinyl ester, or polyacrylate.

Embodiment 11: The sensor of any one of Embodiments 1-10, wherein the biodegradable target includes an oligo- or polysaccharide and comprises one or more of cellulose, cellobiose, hemicellulose, cellulose derivative, xylooligosaccharide (XOS), fructooligosaccharide (FOS), galactooligosaccharide (GOS), isomaltooligosaccharide (IMO), inulin, chitin, chitosan, alginate, carrageenan, or starch-based polymer.

Embodiment 12: The sensor of any one of Embodiments 1-11, wherein the biodegradable target includes a wax and comprises one or more of paraffin wax, beeswax, or soy wax.

Embodiment 13: The sensor of any one of Embodiments 1-12, wherein the biodegradable target includes a fatty acid or ester thereof comprising palmitate.

Embodiment 14: The sensor of any one of Embodiments 1-13, wherein the biodegradable target includes an alkane selected from nonacosane, hexadecane, or octadecane.

Embodiment 15: The sensor of any one of Embodiments 1-14, wherein the biodegradable target includes a polyester and comprises one or more of polycaprolactone (PCL), polyethylene terephthalate (PET), polylactic acid (PLA), or polyglycolic acid (PGA).

Embodiment 16: The sensor of any one of Embodiments 1-15, wherein the biodegradable target includes a polyvinyl ester and comprises one or both of polyvinyl acetate or polyvinyl propionate.

Embodiment 17: The sensor of any one of Embodiments 1-16, wherein the biodegradable target includes a polyacrylate and comprises one or more of polymethyl acrylate, polyethyl acrylate, or polybutyl acrylate.

Embodiment 18: The sensor of any one of Embodiments 1-17, wherein the biodegradable target includes a copolyester and comprises poly(butylene adipate-co-butylene furandicarboxylate).

Embodiment 19: The sensor of any one of Embodiments 1-18, wherein the biodegradable target comprises one or more petroleum hydrocarbons.

Embodiment 20: The sensor of any one of Embodiments 1-19, wherein the biodegradable target comprises one or more of cotton or paper.

Embodiment 21: The sensor of any one of Embodiments 1-20, wherein the conductive particles comprise carbon particles.

Embodiment 22: The sensor of any one of Embodiments 1-21, wherein the conductive particles comprise metal particles.

Embodiment 23: The sensor of any one of Embodiments 1-22, wherein the conductive particles comprise tungsten, zinc, magnesium, or iron particles.

Embodiment 24: The sensor of any one of Embodiments 1-23, wherein the conductive trace is positioned in a curved shape.

Embodiment 25: The sensor of Embodiment 24, wherein the conductive trace forms a "U" shape.

Embodiment 26: A system for measuring enzyme activity in a measurement environment, the system comprising two or more enzyme activity sensors, each independently as in any one of Embodiments 1-25.

Embodiment 27: The system of Embodiment 26, wherein the system comprises an enzyme sensor panel comprising multiple different enzyme sensors configured to sense a different enzyme or combination of enzymes.

Embodiment 28: The system of Embodiment 26 or 27, further comprising a power source coupled to the one or more enzyme activity sensors.

Embodiment 29: The system of any one of Embodiments 26-28, wherein the power source comprises a solar panel.

Embodiment 30: The system of any one of Embodiments 26-29, further comprising a controller in electrical communication with the one or more enzyme activity sensors, the controller being configured to deliver electrical current to the one or more enzyme activity sensors and measure resulting resistance.

Embodiment 31: The system of Embodiment 30, further comprising a communications module communicatively connected to the controller and configured to connect to a network to enable transfer of sensor data and/or receipt of system instructions.

Embodiment 32: The system of Embodiment 31, wherein the network is a cellular network or a satellite network.

Embodiment 33: A method of measuring enzyme activity, the method comprising: providing an enzyme activity sensor as in any one of Embodiments 1-25 or a system as in any one of Embodiments 26-32, the biodegradable target of the enzyme activity sensor being configured to degrade in the presence of one or more target enzymes; positioning the enzyme activity sensor in a measurement environment having or suspected of having the one or more target enzymes; measuring resistance in the conductive trace of the enzyme activity sensor; determining that the resistance has reached a threshold level indicative of enzymatic degradation of the biodegradable target of the enzyme activity sensor; and based on the time to reach the threshold level indicative of enzymatic degradation of the biodegradable target, determine a level of the one or more target enzymes in the measurement environment.

Embodiment 34: The method of Embodiment 33, wherein the one or more target enzymes comprise cellobiohydrolase, β-glucosidase, β-xylosidase, phenol oxidase, peroxidase, chitinase, chitin deacetylase, urease, phosphatase, cutinase, PHB-depolymerase, lipase, lipolase, pancrease, xanthine oxidase, catalase, esterase, pullulanase, or amylase.

Additional Terms & Definitions

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, less than 1%, less than 0.1%, or less than 0.01% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may also include properties and/or features (e.g., ingredients, components, members, elements, parts, and/or portions) described in one or more separate embodiments and are not necessarily limited strictly to the features expressly described for that particular embodiment. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

The invention claimed is:

1. A sensor configured for measuring enzyme activity corresponding to true in situ enzyme activity levels, the sensor comprising:
   a degradable conductive trace that includes
      a first terminal end, a second terminal end, and an intermediate section disposed between the first and second terminal ends, the intermediate section including conductive particles disposed therein,
      a biodegradable target configured to enable the conductive trace, in an initial state, to conduct electrical current between the first and second terminal ends via the conductive particles, and
   wherein at least the intermediate section is configured to degrade over time as a result of in situ enzymatic activity of a target microorganism or group of microorganisms that degrades the biodegradable target when the sensor is placed in a measurement environment, the enzymatic activity thereby increasing resistance between the first and second terminal ends,
   wherein at least the intermediate section omits overlying layers such that the biodegradable target is directly exposed to the target microorganism or group of microorganisms when placed in the measurement environment; and
   a support upon which the conductive trace is disposed.

2. The sensor of claim 1, wherein the biodegradable target comprises a binder in which the conductive particles are disposed, the binder being formed from a biodegradable material that degrades over time when exposed to one or more enzymes that act upon the biodegradable material.

3. The sensor of claim 2, wherein the binder is not water-soluble.

4. The sensor of claim 3, wherein the binder includes an oligo- or polysaccharide and comprises one or more of cellulose, cellobiose, hemicellulose, cellulose derivative, xylooligosaccharide (XOS), fructooligosaccharide (FOS), galactooligosaccharide (GOS), isomaltooligosaccharide (IMO), inulin, chitin, chitosan, alginate, carrageenan, or starch-based polymer.

5. The sensor of claim 2, wherein the binder absorbs water and swells when exposed thereto.

6. The sensor of claim 2, wherein the binder comprises one or more of a lignin, oligo- or polysaccharide, wax, polyhydroxyalkanoate, fatty acid or fatty acid ester, alkane, polyester, copolyester, polyurethane, polyvinyl ester, or polyacrylate.

7. The sensor of claim 2, wherein the binder includes a wax and comprises one or more of paraffin wax, beeswax, or soy wax.

8. The sensor of claim 2, wherein the binder includes a fatty acid or ester thereof comprising palmitate.

9. The sensor of claim 2, wherein the binder includes an alkane selected from nonacosane, hexadecane, or octadecane.

10. The sensor of claim 2, wherein the binder includes a polyester and comprises one or more of polycaprolactone (PCL), polyethylene terephthalate (PET), polylactic acid (PLA), or polyglycolic acid (PGA).

11. The sensor of claim 2, wherein the binder includes a polyvinyl ester and comprises one or both of polyvinyl acetate or polyvinyl propionate.

12. The sensor of claim 2, wherein the binder includes a polyacrylate and comprises one or more of polymethyl acrylate, polyethyl acrylate, or polybutyl acrylate.

13. The sensor of claim 2, wherein the binder includes a copolyester and comprises poly(butylene adipate-co-butylene furandicarboxylate).

14. The sensor of claim 2, wherein the binder comprises one or more petroleum hydrocarbons.

15. The sensor of claim 2, wherein the binder comprises one or more of cotton or paper.

16. The sensor of claim 1, wherein the conductive particles comprise carbon particles.

17. The sensor of claim 1, wherein the conductive particles comprise metal particles.

18. The sensor of claim 17, wherein the conductive trace forms a "U" shape.

19. The sensor of claim 1, wherein the conductive particles comprise tungsten, zinc, magnesium, or iron particles.

20. The sensor of claim 1, wherein the conductive trace is positioned in a curved shape.

21. A system for measuring enzyme activity in a measurement environment, the system comprising one or more enzyme activity sensors as in claim 1.

22. The system of claim 21, wherein the system comprises an enzyme sensor panel comprising multiple different enzyme sensors configured to sense a different enzyme or combination of enzymes.

23. The system of claim 21, further comprising a power source coupled to the one or more enzyme activity sensors.

24. The system of claim 23, wherein the power source comprises a solar panel.

25. The system of claim 21, further comprising a controller in electrical communication with the one or more enzyme activity sensors, the controller being configured to deliver electrical current to the one or more enzyme activity sensors and measure resulting resistance.

26. The system of claim 25, further comprising a communications module communicatively connected to the controller and configured to connect to a network to enable transfer of sensor data and/or receipt of system instructions.

27. The system of claim 26, wherein the network is a cellular network or a satellite network.

28. A method of measuring enzyme activity, the method comprising:
providing an enzyme activity sensor as in claim 1, the biodegradable target of the enzyme activity sensor being configured to degrade in the presence of one or more target enzymes;
positioning the enzyme activity sensor in a measurement environment having or suspected of having the one or more target enzymes;
measuring resistance in the conductive trace of the enzyme activity sensor;
determining that the resistance has reached a threshold level indicative of enzymatic degradation of the biodegradable target of the enzyme activity sensor; and
based on the time to reach the threshold level indicative of enzymatic degradation of the biodegradable target, determine a level of the one or more target enzymes in the measurement environment.

29. The method of claim 28, wherein the one or more target enzymes comprise cellobiohydrolase, β-glucosidase, β-xylosidase, phenol oxidase, peroxidase, chitinase, chitin deacetylase, urease, phosphatase, cutinase, PHB-depolymerase, lipase, lipolase, pancrease, xanthine oxidase, catalase, esterase, pullulanase, or amylase.

* * * * *